US005727071A

United States Patent [19]

Suzuki

[11] Patent Number: 5,727,071

[45] Date of Patent: Mar. 10, 1998

[54] NOISE SILENCING DEVICE

[75] Inventor: Mitsuharu Suzuki, Tokyo, Japan

[73] Assignee: NEC Corporation, Tokyo, Japan

[21] Appl. No.: 593,685

[22] Filed: Jan. 29, 1996

[30] Foreign Application Priority Data

Jan. 27, 1995 [JP] Japan .................................... 7-011344

[51] Int. Cl.[6] ........................................ A61F 11/06

[52] U.S. Cl. ................................. 381/71.8; 381/71.1

[58] Field of Search .............................. 381/71, 73.1, 94, 381/71.1, 71.2, 71.4, 71.5, 71.8, 71.13, 71.14, 94.1, 94.9

[56] References Cited

U.S. PATENT DOCUMENTS

| | | | |
|---|---|---|---|
| 4,805,733 | 2/1989 | Kato et al. | 381/71 |
| 5,319,715 | 6/1994 | Nagami et al. | 381/71 |

FOREIGN PATENT DOCUMENTS

| | | |
|---|---|---|
| 342999 | 2/1991 | Japan . |

*Primary Examiner*—Curtis Kuntz
*Assistant Examiner*—Vivian Chang
*Attorney, Agent, or Firm*—Sughrue, Mion, Zinn, Macpeak & Seas, PLLC

[57] ABSTRACT

A noise silencer is proposed that is composed of a sensor microphone, a speaker, and a control circuit, and which principally silences noise generated from the outside. Noise emitted from a noise source is detected by the sensor microphone, and additional sound for canceling the noise emitted from a noise source is generated from the speaker. The control circuit produces drive signals based on signals from the sensor microphone for causing the generation of additional sound from the speaker that is of reverse phase and identical sound pressure with respect to noise emitted from the noise source.

2 Claims, 1 Drawing Sheet

NOISE SILENCING DEVICE

BACKGROUND OF THE INVENTION:

1. Field of the Invention

The present invention relates to a noise silencing device, and particularly to a noise silencing device for silencing exterior noise originating from airports, railways, or heavily traveled roads.

2. Description of the Related Art

A silencing device of this type is disclosed in Japanese Patent Laid-open No. 42999/91. This silencer is immovably installed and, as one constituent element, is provided with detection means (for example, an error microphone) that detects sound waves after sound wave interference occurs between noise and additional sound.

The above-described silencer of the prior art is immovably installed and therefore exhibits no effect against moving sources of noise such as airplanes, trains, or automobiles, and as an indispensable constituent element in addition to the noise detection means, must additionally be provided with detection means for detecting sound waves after interference between noise and additional sound.

SUMMARY OF THE INVENTION

The object of the present invention is to provide a noise silencer that is effective against mobile sources of noise and moreover, has an easily mobile and simple structure that does not include detection means for inference waves.

To achieve the above-described object, the noise silencer according to the present invention includes:

noise information detection means for detecting information of noise emitted from a noise source; additional sound generating means for generating additional sound for canceling noise emitted from the noise source; and control means for producing drive signals based on signals from the noise information detection means to cause the additional sound generator to generate additional sound having reverse phase as well as identical sound pressure with respect to noise emitted from the noise source.

The present invention enables cancellation of various noise emitted from the outside, and can dispense with a means such as an error microphone used in the prior art for assessing the silencing effect after interference occurs between noise waves and additional sound waves.

According to one embodiment of the present invention, the control means includes A/D conversion means for converting noise signals detected by the noise information detection means to digital signals; frequency detection means for detecting frequency of noise detected by the noise information detection means; delay means for calculating a delay time by a prescribed calculation formula from the noise frequency and from the distance between the noise information detection means and the additional sound generating means such that additional sound generated from the additional sound generating means is of exactly reversed phase with respect to noise reaching the additional sound generating means and delaying for the delay time the output signals of the A/D conversion means; and D/A conversion means for converting output signals of the delay means to analog signals and outputting the result to the additional sound generating means as drive signals.

According to another embodiment of the present invention, the above-described delay time ΔD can be found using the calculation formula:

$$\Delta D = L/V + ½f - L/C$$

where L is the distance between the noise information detection means and the additional sound generating means, V is the speed of the noise waves, f is the frequency of the noise waves, and C is the speed of light.

According to yet another embodiment of the present invention, the delay means includes means for correcting the amount of fluctuation of the delay time due to temperature.

The above and other objects, features, and advantages of the present invention will become apparent from the following description with references to the accompanying drawings which illustrate an examples of the present invention.

DETAILED DESCRIPTION OF THE PREFERRED EMBODIMENTS

Figure 1:
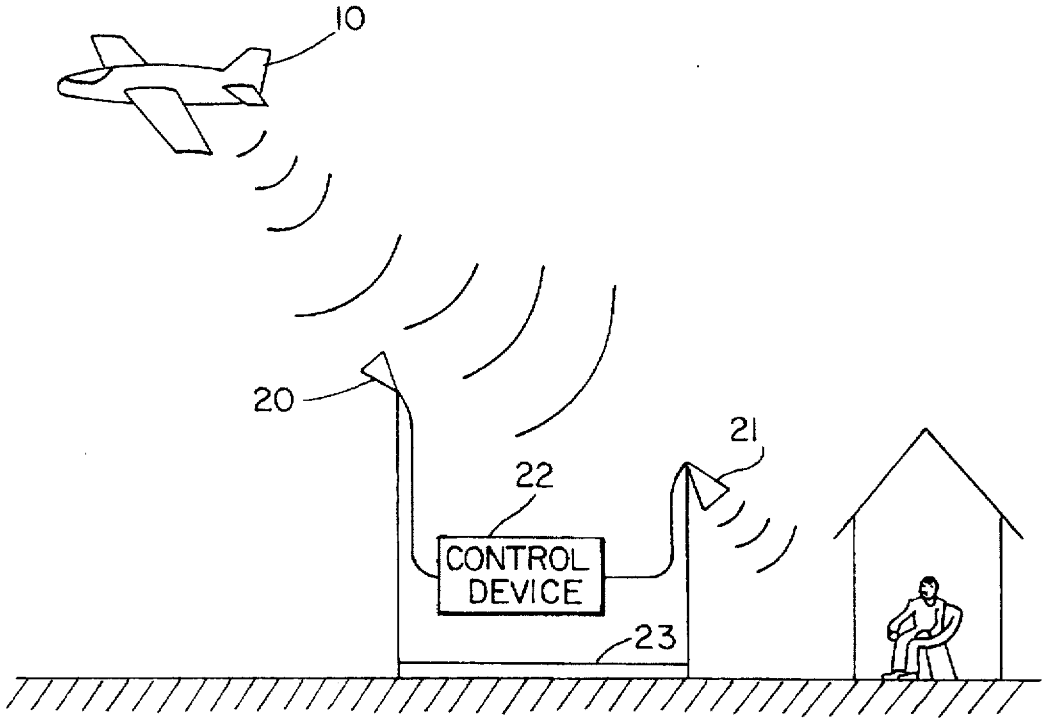
FIG. 1 shows the construction of a noise silencer according to an embodiment of the present invention.

Referring to FIG. 1, the noise silencer of the present invention silences noise emitted from a noise source 10, and is made up of a sensor microphone 20 as a noise information detection means; a speaker 21 as an additional sound generating means; a control device 22 for outputting drive signals to speaker 21 based on output signals of sensor microphone 20; and coupling rod 23 for connecting sensor microphone 20 and speaker 21 at a fixed distance.

Sensor microphone 20 detects noise emitted from noise source 10 and outputs the detection signal to control device 22. Speaker 21 is established at a position closer to the receiving side (for example, a person) of noise than to noise source 10 with respect to sensor microphone 20, and generates additional sound for canceling noise emitted from noise source 10 according to drive signals from control device 22.

Figure 2:
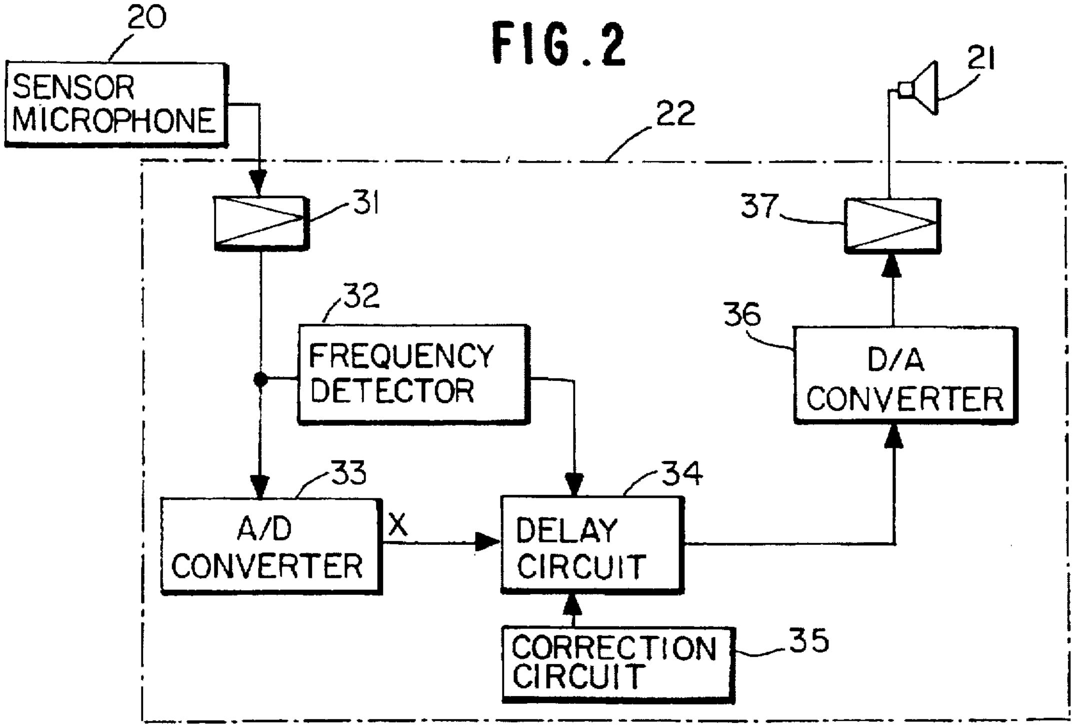
FIG. 2 is a block diagram showing the construction of control circuit 23 of FIG. 1.

Referring to FIG. 2, control device 22 is made up of amplifier 31, frequency detector 32, A/D converter 33, delay circuit 34, correction circuit 35, D/A converter 36, and amplifier 37.

Signal X, which indicates noise detected by sensor microphone 20 and outputted by way of amplifier 31 and A/D converter 33, is inputted to delay circuit 34. In addition, a signal representing the frequency of the noise is also inputted to delay circuit 34 by way of amplifier 31 and frequency detector 32.

Delay circuit 34 determines the delay time ΔD to be added to input signal X based on the frequency of the noise obtained from frequency detector 32 and the predetermined length of coupling rod 23 joining sensor microphone 20 with speaker 21 and through its own calculation formula such that the additional sound generated from speaker 21 is of exactly reversed phase with respect to noise reaching speaker 21, and delays input signal X for exactly that delay time ΔD.

The calculation formula incorporated in delay circuit 34 is as follows:

$$\Delta D = L/V + ½f - L/C$$

where L is the length of coupling rod 23, V is the speed of noise waves (sound waves); f is the frequency of the noise waves; and C is the speed of an electron (the speed of light).

In this case, L/V is the time required for noise waves to travel from the position of sensor microphone 20 to the position of speaker 21, and is a fixed value assuming that the speed of sound is approximately fixed. ½ f is the time required for noise waves of frequency f to progress ½ wavelength. L/C represents the time for noise wave signals received at sensor microphone 20 to be outputted from speaker 21, and is virtually negligible compared to L/V and ½ f.

The output signals of this delay circuit 34 are D/A converted by D/A converter 36, proceed through amplifier 37, and are outputted to speaker 21 for emitting silencing sound waves.

In this way, signal X, which indicates noise based on a frequency signal of noise waves obtained at frequency detector 32, is delayed exactly ΔD by delay circuit 34, and the phase of canceling sound waves outputted from speaker 21 is always the reverse phase with respect to the noise waves, thereby canceling sound waves propagated from noise source 10.

Furthermore, the speed of propagated sound waves varies according to temperature, and in consideration of the amount of fluctuation due to the temperature, delay circuit 34 is provided with correction circuit 35 for correcting delay time by regulating the value of L/V.

In the above-described embodiment, a coupling rod 23 was used as a means of joining and maintaining a fixed distance between sensor microphone 20 and speaker 21, but any metallic wiring material may be used that does not cause expansion or shrinkage of the distance.

While a preferred embodiment of the present invention has been described using specific terms, such description is for illustrative purposes only, and it is to be understood that changes and variations may be made without departing from the spirit or scope of the following claims.

What is claimed is:

1. A noise silencer comprising:

noise information detection means for detecting information of noise emitted from a noise source;

additional sound generating means for generating additional sound for canceling noise emitted from said noise source; and control means comprising A/D conversion means for converting noise signals detected by said noise information detection means into digital signals;

frequency detection means for detecting a frequency of noise detected by said noise information detection means;

delay means for calculating a delay time by a prescribed calculation formula from said noise frequency and from a distance between said noise information detection means and said additional sound generating means such that additional sound generated from said additional sound generating means is exactly reversed in phase with respect to noise reaching said additional sound generating means and delaying for said delay time output signals of said A/D conversion means; and D/A conversion means for converting output signals of said delay means to analog signals and outputting the result to said additional sound generating means as drive signals;

wherein said delay time ΔD is found using calculation formula:

$$\Delta D = L/V + \tfrac{1}{2}f - L/C$$

where L is the distance between said noise information detection device and said additional sound generating device, V is the speed of noise waves, f is the frequency of noise waves, and C is the speed of light.

2. A noise silencer comprising:

a noise information detection device which detects information of noise emitted from a noise source;

an additional sound generating device which generates additional sound for canceling noise emitted from said noise source; and a control circuit comprising an A/D conversion circuit which converts noise signals detected by said noise information detection device into digital signals;

a frequency detection circuit which detects a frequency of noise detected by said noise information detection device;

a delay circuit which calculates a delay time by a prescribed calculation formula from said noise frequency and from a distance between said noise information detection means and said additional sound generating means such that additional sound generated from said additional sound generating means is exactly reversed in phase with respect to noise reaching said additional sound generating means, said delay circuit delaying for said delay time output signals of said A/D conversion means; and a D/A conversion circuit which converts output signals of said delay circuit to analog signals and outputs the result to said additional sound generating means as drive signals;

wherein said delay time ΔD is found using calculation formula:

$$\Delta D = L/V + \tfrac{1}{2}f - L/C$$

where L is the distance between said noise information detection device and said additional sound generating device, V is the speed of noise waves, f is the frequency of noise waves, and C is the speed of light.

* * * * *